United States Patent
Santhanam

(10) Patent No.: US 12,053,484 B2
(45) Date of Patent: Aug. 6, 2024

(54) SIMETHICONE CHEWABLE COMPOSITION

(71) Applicant: MEDICATED CHEWS, LLC, East Hanover, NJ (US)

(72) Inventor: Karthikeyan Santhanam, Basking Ridge, NJ (US)

(73) Assignee: MEDICATED CHEWS, LLC, East Hanover, NJ (US)

( * ) Notice: Subject to any disclaimer, the term of this patent is extended or adjusted under 35 U.S.C. 154(b) by 0 days.

(21) Appl. No.: 17/930,261

(22) Filed: Sep. 7, 2022

(65) Prior Publication Data

US 2023/0136537 A1  May 4, 2023

Related U.S. Application Data

(60) Provisional application No. 63/263,276, filed on Oct. 29, 2021.

(51) Int. Cl.
*A61K 31/80* (2006.01)
*A61K 9/00* (2006.01)

(52) U.S. Cl.
CPC ............ *A61K 31/80* (2013.01); *A61K 9/0056* (2013.01)

(58) Field of Classification Search
None
See application file for complete search history.

(56) References Cited

U.S. PATENT DOCUMENTS

| | | | |
|---|---|---|---|
| 4,327,076 A | 4/1982 | Puglia et al. | |
| 4,327,077 A | 4/1982 | Puglia et al. | |
| 5,637,313 A * | 6/1997 | Chau ...................... | A61K 31/52 424/440 |
| 6,077,524 A | 6/2000 | Bolder et al. | |
| 10,617,714 B2 | 4/2020 | Stella et al. | |
| 10,722,472 B2 | 7/2020 | McNally et al. | |
| 11,154,495 B2 | 10/2021 | Romanoschi et al. | |
| 2010/0272781 A1 | 10/2010 | Subramanian et al. | |
| 2012/0164134 A1 | 6/2012 | Davis | |
| 2019/0099379 A1 * | 4/2019 | McNally ................ | A61K 9/501 |
| 2019/0364924 A1 | 12/2019 | Capdepon et al. | |
| 2019/0388341 A1 * | 12/2019 | Simpson ................ | A61K 47/12 |
| 2020/0022909 A1 * | 1/2020 | Dixit ...................... | A61K 47/36 |

FOREIGN PATENT DOCUMENTS

| | | |
|---|---|---|
| EP | 0858801 A1 | 8/1998 |
| EP | 1957110 B1 | 9/2020 |
| KR | 20040026843 A | 4/2004 |
| WO | 8807862 A1 | 10/1988 |
| WO | 9618387 A1 | 6/1996 |
| WO | 2005048974 A2 | 6/2005 |
| WO | 2005048975 A1 | 6/2005 |
| WO | 2008073517 A1 | 6/2008 |
| WO | 2016154503 A1 | 9/2016 |
| WO | 2016164470 A1 | 10/2016 |
| WO | 2021014426 A1 | 1/2021 |
| WO | 2021059082 A1 | 4/2021 |
| WO | 2022259255 A1 | 12/2022 |

OTHER PUBLICATIONS

The United States Pharmacopeial Convention, "<905> Uniformity of Dosage Units," General Chapter, Stage 6 Harmonization:1-3 (2011).
Davydova N., "USP Chewable Gels Monographs," The United States Pharmacopeial Convention, Web page <https://www.usp.org/sites/default/files/usp/document/stakeholder-forum/chewable-gels.pdf> Date Accessed Jan. 18, 2024.
Davydova N., "Overview of USP Monographs for Chewable Gels (Marketed as Gummies)," The United States Pharmacopeial Convention, Oct. 30, 2023.

* cited by examiner

Primary Examiner — Patricia Duffy
Assistant Examiner — Garen Gotfredson
(74) Attorney, Agent, or Firm — MEDLER FERRO WOODHOUSE & MILLS PLLC

(57) ABSTRACT

The invention relates to a chewable medicated composition comprising simethicone as the sole active ingredient, and at least one gelling agent.

7 Claims, No Drawings

SIMETHICONE CHEWABLE COMPOSITION

FIELD OF THE INVENTION

The invention relates to a chewable medicated composition comprising simethicone as the sole active ingredient, and at least one gelling agent.

BACKGROUND

Chewable medicated compositions, also known as gummies, gummy bears, gum drops, jelly candy, gummi chews, chewable gels, chew gels, soft chews, gummy candy, gummies, jelly fruit candy, confectionery or jellies consist of gelling component(s) such as starch, gelatin, gluten, pectin and other binding agents of these kind. These dosage forms are intended to be chewed before being swallowed, and may contain one or more active ingredients. Major ingredients of commercially available gummies include gelatin or pectin or agar (5-8%), water (15-20%), sucrose (28-50%), and corn syrup solids (40-55%). Typically, mass production involves use of gelatin base that is mixed and cooked in a cooker under steam and pressure, followed by mixing the cooked gelatin with flavors, colors, acids, fruit concentrates, active ingredients (if any). This is then followed by pumping the cooked gelatin stock into starch filled mould boards, also known as a mogul, to obtain desired shapes. The shaped candies are then cured to obtain the final product.

The commercially available gummies are almost always obtained using gelatin and the process described above, i.e. using a mogul. Thus, the starch used is a huge source of contamination and a major issue in maintaining clean facilities, thereby making it difficult to meet regulatory requirements on good manufacturing practices. Further, use of gelatin and starch requires the use of a consistent and high drying temperature, which makes it difficult to use for active ingredients and excipients that are thermolabile. The disadvantages of starch in manufacturing of gummies is further described in United States Patent publication 20190364924, which is incorporated herein by reference.

Further, gummies containing starches with a high amylose content have a pronounced brittleness, especially in comparison with candy based on gelatin. At higher water contents (that is, at higher relative humidities), as well as at an elevated temperature (summer), such gummy becomes very soft and tends to deliquesce. At low water contents (that is, at low relative humidities) as well as at lower temperatures (winter) such gummy becomes comparatively hard.

A major disadvantage of gelatin is its solubility. It dissolves as a colloidal sol at temperatures at or above 37° C., and gels at lower temperatures around room temperature. Gelatin can cause an unpleasant taste, feeling of heaviness in the stomach, bloating, heartburn, and belching, all of which add to the discomfort of a person already experiencing flatulence and gastric discomfort. Gelatin can also cause allergic reactions. Also, in accordance with the general trend in the direction away from animal products, gelatin-free candy is increasingly being demanded by the consumer.

Several gummies or chewable compositions are now available on the market that contain active ingredients and are dispensed over the counter (OTC). The present invention provides a chewable gummy composition containing simethicone as the sole active ingredient, which is free of gelatin and gluten, and is substantially sugar free. The compositions of the present invention contain 125 mg simethicone per unit or per chew, and contains at least one gelling agent.

Commercially available simethicone preparations are in the form of tablets, chewable tablets, soft gelatin capsules, oral liquids such as suspension drops and emulsions. While gummies containing simethicone have been reported in the art, there is no commercially available gummy, nor a prior publication that provides gummies containing simethicone as the sole active ingredient.

Some patent publications seen were as follows—
KR20040026843, in the name of Lee Yong Won, provides hard chewing candy comprising nicotine in combination with an active ingredient for mitigating adverse reactions caused by smoking cessation, like simethicone.

U.S. Ser. No. 10/722,472B2, in the name of Johnson and Johnson, relates to microencapsulated simethicone particles containing simethicone and a water-soluble coating comprising gelatin. It does not disclose a gummy composition with simethicone uniformly dispersed in the carrier vehicle that is free of gelatin.

U.S. Ser. No. 10/617,714 B2, in the name of Procter and Gamble Co, relates to an effervescent chewable dosage form of simethicone, but does not disclose a gummy composition containing simethicone.

In order to overcome disadvantages associated with traditionally used agents such as gelatin and starch, and in order to improve patient compliance there exists a need to develop stable gummy compositions or medicated chews that are substantially free of gluten and sugar. Such gummy compositions would be advantageous over conventionally available dosage forms of simethicone in terms of ease of administration for paediatric and geriatric patients, and for patients with dental challenges who prefer not to eat candies and preparations that have high sugar content. The high sugar content can also be a cause for concern in patients with gastric discomfort and those with diabetes. The simethicone containing gummies certainly have advantages over pediatric suspension and emulsion dosage forms in that they are easy to carry and administer, and there are no issues of spillage as well as under or over-dosing.

SUMMARY OF THE INVENTION

The present invention provides a chewable medicated composition comprising simethicone as the sole active ingredient, and at least one gelling agent. The chewable medicated compositions of the invention are stable, non-sticky and crispy in texture.

In a preferred embodiment, the chewable medicated composition of the present invention containing simethicone as the sole active ingredient is free of gelatin, and is substantially free of starch, sugar and gluten.

In one embodiment, the chewable medicated composition comprises simethicone as the sole active ingredient, at least one gelling agent, at least one sweetening agent, a pH adjusting agent, flavouring agent, one or more dietary fiber and a coloring agent, wherein the composition is substantially free of sugar, and does not contain gelatin or gluten.

In one embodiment, the chewable medicated composition containing simethicone has a content uniformity that meets the requirements of the USP <905> Uniformity of Dosage Units test.

In another embodiment, the chewable medicated composition containing simethicone disintegrates within about 40 minutes or less when tested using the USP <701> Disintegration Test.

The present invention also provides a method of forming the chewable medicated composition which comprises the steps of (a) manufacturing the mass, (b) drying the mass, and (c) coating the mass with wax, wherein the process is free of use of gelatin and mogul.

In another preferred embodiment of the present invention, the chewable medicated composition contains simethicone as the sole antiflatulent or antigas agent, and the maximum daily dose of simethicone does not exceed 500 mg.

In another embodiment, the chewable medicated composition of the present invention contains simethicone as the sole active ingredient for alleviating or relieving the symptoms referred to as gas.

In one embodiment, the chewable medicated composition contains simethicone as the sole active ingredient, and the composition meets all the FDA requirements for OTC monograph products for Simethicone under Section 332.10.

DETAILED DESCRIPTION OF THE INVENTION

Simethicone is a silicone compound used for the management of flatulence and bloating. It relieves the discomfort produced by the presence of excess gas in the gastrointestinal tract. It acts in the stomach and intestines to change the surface tension of gas bubbles, enabling their breakdown and the formation of larger bubbles. In this way it is believed that gas can be eliminated more easily by belching or passing flatus. It was first approved by the USFDA in 1952. It is available in the form of tablets, soft gelatin capsules, hard gelatin capsules and oral liquid. The chemical name for simethicone is α-(trimethylsilyl)-ω-methylpoly[oxy(dimethylsilylene)], mixture with silicon dioxide.

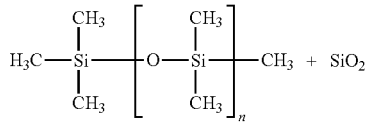

The simethicone products are usually available OTC, and are indicated for alleviating or relieving symptoms such as bloating, pressure, fullness or stuffed feeling, commonly referred to as gas. Some off-label uses of simethicone include (1) symptomatic relief of functional dyspepsia, (2) use as an aid in gastrointestinal or bowel preparation, (3) to reduce foaming and enhance visualization during endoscopy, colonoscopy, gastrointestinal radiography, or other GI diagnostic procedures. Simethicone has a long history of use in gastrointestinal (GI) diagnostic procedures. Single dose of 40 mg to 133 mg given orally, 20 minutes to 1 hour prior to various endoscopy, colonoscopy, or GI radiographic procedures is most common. Most publications/guidelines agree that the addition of simethicone prior to standard preparation regimens may aid visualization during magnetically controlled capsule endoscopy, upper gastroscopy or endoscopy, colonoscopy, GI radiography, and selected other GI procedures. The effect on diagnostic yield is controversial. Also, simethicone residue despite endoscope reprocessing has been reported.

Each simethicone chewable medicated composition of the present invention contains 125 mg of simethicone. The dose of simethicone per day does not exceed 500 mg, and can be given once per day or multiple times per day in the form of divided doses given twice, thrice or four times a day at bedtime as needed (non-prescription dosing), or as directed by a physician.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rendering the therapy ineffective. Further, solid dosage forms are not recommended for children or elderly due to increased risk of choking.

The chewable medicated compositions of the present invention containing simethicone are thus convenient for use in pediatric patients of age 5 years and above, geriatric patients who have anxiety over swallowing pills, tablets or capsules, and in patients suffering from dysphagia. The convenience of having the simethicone composition in the form of a soft chewable composition helps increase compliance. Further, since the chewable medicated composition of the invention is free of gelatin, it is convenient for use in vegetarian and vegan individuals who avoid animal origin products. The compositions of the present invention are also substantially free of sugar, thereby making them helpful and advantageous for patients with diabetes, those wanting to keep sugar consumption low and in children and/or individuals that may have dental issues such as cavities.

The chewable medicated compositions described herein do not require gelatin as the gelling agent. The compositions are also free of gluten. The present inventors set out to provide a plant-based gelling agent that can fully replace animal-derived products like gelatin, such that the final product is suitable not only for vegetarians, vegans or religious groups, but also for those suffering (even without knowing) from a celiac disease. Furthermore, they aimed at using a natural source with a reliable availability, and one that is economically viable. In particular, the chewable medicated compositions of the present invention are aimed at providing gelatin-free and gluten-free chewable compositions that display elasticity, texture profile and mouthfeel comparable or better than that of the standard gelatin based gummies.

The chewable medicated compositions of the present invention comprise simethicone as the sole active ingredient, and one or more excipients selected from gelling agents, sweetening agents, pH adjusting agents, dietary fibers, flavouring agents and coloring agents.

The chewable medicated composition comprises an effective amount of simethicone in the range of about 5% w/w to about 30% w/w of the total composition. In preferred embodiments, simethicone is present in the range of about 5% w/w to about 20% w/w, preferably in the range of about 5% w/w to about 15% w/w, more preferably in the range of about 5% w/w to about 10% w/w of the total composition. The chewable medicated composition comprises simethicone in an amount ranging from about 125 mg to about 250 mg, which may be provided in the form of one or two serving sizes.

Simethicone active ingredient may be used in the form of an emulsion that is added to the other excipients and formulated into the chewable medicated composition. Typically, Simethicone emulsion, USP may be used. Simethicone Emulsion is a water-dispersible form of Simethicone composed of Simethicone, suitable emulsifiers, preservatives, and water. It may contain suitable viscosity-increasing agents. The Simethicone emulsion contains an amount of polydimethylsiloxane ([—(CH3)2SiO—]n) that is NLT 85.0% and NMT 110.0% of the labeled amount of simethicone.

Gelling agents are gel-forming agents which dissolve in a liquid phase to form a colloidal mixture that forms a weakly cohesive internal structure in a composition. They are organic hydrocolloids or hydrophilic inorganic substances. Suitable gelling agents include, but are not limited to, carrageenan, pectin and combinations thereof.

Examples of carrageenan that may be used may include kappa (k) carrageenans, Iota carrageenan and lambda (l) carrageenan. In one embodiment, the carrageenan used is a free flowing powder having a gel strength ranging between 400 to 1300 $g/cm^2$ (when measured for a 1.5% solution in IPA with a 1 $cm^2$ probe), moisture content of not more than 12%, pH ranging between 7 to 12, particle size such that not less than 80% particles pass through USS #100 mesh, and has aerobic plate count of less than 1000 cfu/g and total coliforms less than 500 cfu/g. In another embodiment, the carrageenan used is a free flowing powder having a gel strength ≥800 $g/cm^2$ (when measured for a 1.5% solution in IPA with a 1 $cm^2$ probe), moisture content of not more than 12%, pH ranging between 7 to 10, particle size such that 95% particles pass through USS #80 mesh, and has aerobic plate count of less than 5000 cfu/g and total coliforms less than 100 cfu/g.

Pectins that may be used are also known as citrus pectin, methopectin, methyl pectin, methyl pectinate, mexpectin, pectina or pectinic acid. Pectin is a purified carbohydrate product obtained from the dilute acid extract of the inner portion of the rind of citrus fruits or from apple pomace. It consists chiefly of partially methoxylated polygalacturonic acids. It is used as a gelling agent in the chewable medicated compositions of the present invention either alone or in combination with carrageenan, but more preferably in combination with carrageenan. When the chewable medicated composition of the present invention includes a mixture of carrageenan and pectin as a gelling agent, the two agents are present in a ratio ranging from about 10:90 to about 90:10. In preferred embodiments, carrageenan and pectin are used in a ratio of about 90:10. In still more preferred embodiments, carrageenan and pectin are used in a ratio of about 80:20. In still more preferred embodiments, carrageenan and pectin are used in a ratio of about 70:30 by total weight of the composition.

The gelling agent is typically present in the range of about 0.1% w/w to about 10% w/w of the total composition. Preferably, the gelling agent is present in the range of about 0.1% w/w to about 9% w/w, more preferably in the range of about 0.1% w/w to about 8% w/w, still more preferably in the range of about 0.1% w/w to about 7% w/w, more preferably in the range of about 0.1% w/w to about 6% w/w, more preferably in the range of about 0.1% w/w to about 5% w/w, more preferably in the range of about 0.1% w/w to about 4% w/w, more preferably in the range of about 0.1% w/w to about 3% w/w, more preferably in the range of about 0.1% w/w to about 2% w/w, more preferably in the range of about 0.1% w/w to about 1% w/w of the total composition.

Sweeteners or sweetening agents that may be used in the chewable medicated compositions of the present invention include any compound that provides a sweet taste. This includes nutritive sweetening agents, non-nutritive sweetening agents and mixtures thereof. The nutritive sweetening agents may be selected from, but are not limited to, dextrose, fructose, sucrose, agave nectar, brown rice syrup, date sugar, honey, molasses and blackstrap molasses, sorghum syrup, stevia, maple syrup, birch syrup, yacon syrup, lucuma powder, coconut sugar, erythritol, maltitol, mannitol, sorbitol, xylitol, isomalt, lactitol, and mixtures thereof. The non-nutritive sweetening agents may be selected from, but are not limited to, acesulfame, advantame, alitame, aspartame, neotame, saccharin, sodium saccharin, sucralose, acesulfame potassium, thaumatin, stevioside and mixtures thereof.

The chewable medicated compositions contain sweetening agent in the range of about 10% w/w to about 90% w/w of the total composition. Typically, the sweetening agent is present in the range of about 10% w/w to about 85% w/w, preferably in the range of about 10% w/w to about 80% w/w, more preferably in the range of about 10% w/w to about 75% w/w, still more preferably in the range of about 10% w/w to about 70% w/w of the total composition.

The simethicone chewable medicated composition of the present invention is substantially sugar free, and may contain no added sugar.

The chewable medicated composition may comprise a dietary fiber selected from, but not limited to, inulin, ginger, oligofructose, beta-glucans and the like and mixtures thereof, in the range of about 1% w/w to about 20% w/w of the total composition. In some embodiments, a dietary fiber is present in the range of about 1% w/w to about 19% w/w, more preferably in the range of about 1% w/w to about 18% w/w, more preferably in the range of about 1% w/w to about 17% w/w, more preferably in the range of about 1% w/w to about 16% w/w, more preferably in the range of about 1% w/w to about 15% w/w, more preferably in the range of about 1% w/w to about 14% w/w, more preferably in the range of about 1% w/w to about 13% w/w, more preferably in the range of about 1% w/w to about 12% w/w, more preferably in the range of about 1% w/w to about 11% w/w, more preferably in the range of about 1% w/w to about 10% w/w of the total composition.

Buffering agents are used in the chewable medicated compositions of the present invention to maintain the pH of the simethicone containing composition. Non-limiting examples of buffering agents that may be used include citric acid, malic acid, succinic acid, fumaric acid, tartaric acid, phosphoric acid, boric acid and ascorbic acid, sodium citrate, sodium tartarate, sodium acetate, sodium carbonate, sodium polyphosphate, potassium polyphosphate, sodium pyrophosphate, potassium pyrophosphate, potassium citrate, tripotassium citrate, disodium hydrogen phosphate, dipotassium hydrogen phosphate, trisodium phosphate, trisodium citrate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts and pharmaceutically acceptable salts thereof. In some embodiments, the buffer in the simethicone chewable medicated composition described herein comprises trisodium citrate. In another embodiment, the buffer comprises tripotassium phosphate. In yet another embodiment, tripotassium citrate is used as the buffer. In some embodiments, the buffer used is trisodium phosphate.

The buffering agent(s) is used in an amount such that the chewable medicated composition of the present invention containing simethicone as the sole active ingredient is maintained within a range of about 2.5 to about 6.5.

A flavoring agent or flavorant may be added to enhance the taste or aroma of the chewable medicated composition of the invention. Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, mango, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, Vanilla, winter green, and the like, as well as combinations thereof. Also useful, particularly where the formulation is intended primarily for pediatric use in patients of age 5 years and above, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. In one embodiment, the simethicone chewable medicated composition described herein comprises a mango flavor. In another embodiment, the simethicone chewable medicated composition comprises a ginger flavor. In yet another embodiment, the simethicone chewable medicated composition comprises a grape flavor.

The simethicone chewable medicated compositions may also comprise a coloring agent for identity and/or aesthetic purposes. Suitable coloring agents include natural colors as well as synthetic colors, such as FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide and mixtures thereof. The coloring agent may be present in an amount ranging from about 0.01% w/w to about 2.5% w/w of the total composition. The coloring agent is usually in synchrony with the flavor used in the chewable medicated composition of the present invention. For example, a berry flavored composition may use red or pink color, while a mango flavored composition may use yellow color.

The simethicone chewable medicated compositions of the present invention may be coated with wax to reduce stickiness of the formulation. Wax may be plant or animal-based wax, selected from, but not limited to, organic sunflower seed wax, carnauba wax, soy wax, rice bran wax, candelilla wax, beeswax, and the like and combinations thereof. In preferred embodiments of the invention the simethicone chewable medicated composition is coated with sunflower seed wax. Typically, the seed wax is applied on the moulds before the product is deposited on them, and/or may also be used to polish the finished chewable medicated composition. This not only helps to obtain compositions that are non-sticky, but also provides a crispy texture to the chewable composition.

The simethicone chewable medicated compositions described herein are stable under various storage conditions, including refrigerated, ambient and accelerated conditions. The term "stable", as used herein, refers to chewable medicated composition comprising simethicone as the sole active agent characterized wherein the total microbial count remains <1500 CFU/g when stored for at least 18 months at ambient temperature with minimum exposure to sunlight.

Stable, as used herein, also refers to chewable medicated compositions comprising simethicone as the sole active agent, characterized in that the total heavy metal count remains <1.7 ppm at the end of at least 18 months, when stored at ambient temperature with minimum exposure to sunlight.

At ambient temperature with minimum exposure to sunlight, the simethicone chewable medicated compositions of the present invention are stable for at least 1 month, at least 2 months, at least 3 months, at least 6 months, at least 9 months, at least 12 months, at least 15 months or at least 18 months or over its shelf-life. The term "shelf life" refers to the amount of time the chewable medicated composition are stable (as defined herein) and may be stored without loss of potency and/or performance profile. In some embodiments of the present invention, shelf life refers to the amount of time the chewable medicated composition may be stored without loss of 2%, 5%, 8% or 10% of the potency and/or performance. The stable compositions provided herein are designed to have shelf life of at least 12 months, 24 months or 36 months.

In a particular embodiment, the process of making simethicone chewable medicated composition of the present invention involves the following stages—

Stage 1: Manufacturing the Mass:
  a. Take suitable quantity of water into a cooker and heat it to boiling point (about 100° C. to about 125° C.).
  b. Add gelling agent to step (a) and stir for about 10 to about 15 minutes to get a clear solution.
  c. Add sweetener to step (b) as soon as gelling agent is dissolved (within about 5 to about 30 minutes) and maintain the temperature between about 100° C. to about 120° C.
  d. Add another sweetening agent, and optionally a fiber to step (c) and mix well for at least about 15 to about 20 minutes. Temperature of cooker is maintained between about 70° C. to about 75° C.
  e. Add suitable buffering agent to step (d) and mix well for about 15 to about 30 minutes.
  f. Cook the mass of step (e) until about 65% to about 70% of brix reaches a solid. Heat the mass to a suitable temperature.
  g. Reduce the cooker temperature to about 90° C., and further add suitable quantity of active ingredient, flavouring agent, coloring agent to step (f).
  h. To transfer the mass into hot funnel, open cooker valve. Then activate syrup pump to transfer the mass to holding tank. After that open holding tank valve and activate unloading pump to transfer the mass to hoppers.

Stage 2: Drying the Mass:
  a. Dry the product in qualified drying rooms at a temperature of about 30° C. to about 35° C. with a relative humidity of about 30% to about 35% for about 8 hours to about 72 hours on plastic trays or moulds.

Stage 3: Coating/Waxing the Mass
  a. Transfer the product from plastic trays to coating pan and coat each tray with suitable wax for about 5 to about 15 minutes. After coating, leave the product at room temperature for about 2 to about 24 hours, and then pack the product into bottles or blisters.

The process for making the simethicone chewable medicated compositions of the present invention is critical in obtaining the product with desired properties such as content uniformity, non-sticky crispy texture and stability. Simethicone being a liquid which is temperature sensitive, the addition of the same to the mass is important and must be handled carefully, as described herein. The total quantity of the simethicone may be added to the mass in a single lot, or may be added in divided lots over a period of time. Typically, the amount of simethicone includes about 10% to 15% overages to compensate for any losses during manufacture and storage.

The simethicone chewable medicated compositions of the present invention are typically packaged in inert HDPE bottles with child resistant caps (CRC) of suitable size. Alternatively, they may be packaged in child-resistant blister packs. The packaging may contain additional dessicants to prevent deleterious effects of moisture.

The packaged simethicone chewable medicated compositions possess a content uniformity that meets the requirements of the USP <905> Uniformity of Dosage Units test. The term "uniformity of dosage unit" is defined as the degree of uniformity in the amount of the drug substance among dosage units. The test for "Content Uniformity" of compositions presented in dosage units is based on the assay of the individual content of drug substance(s) in a number of dosage units to determine whether the individual content is within the limits set. The content uniformity is defined by an acceptance value of <15.0, preferably ≤10.0, more preferably <7.5. The "acceptance value" can be determined according to Ph. Eur. 2.9.40/USP<905>. The test is typically carried out by weighing an equal number of units individually to obtain a total of not less than 20 individual weights, and the average weight is calculated. The requirements are met if no individual weight differs from the average weight by more than 7.5%. If 1 unit falls outside of the limits, the procedure is repeated with an additional set of not less than 20 chewable gels. The requirements are met if none of the units tested differ from the average weight by more than 10%.

In some embodiments, the assay of simethicone in the packaged simethicone chewable medicated composition is in the range of about 85% to about 115% (by weight) of the product label claim as determined by USP method for the finished product, and/or as compared to other simethicone dosage forms that may be available on the market.

In another embodiment, the rate of disintegration of the chewable medicated compositions of simethicone is about 60 minutes or less, about 50 minutes or less, about 40 minutes or less. The rate of disintegration of the compositions of the present invention can be measured using various in vitro test methods, for example the USP <701> Disintegration Test.

Definitions

Unless otherwise defined, all technical and scientific terms used herein have the same meaning as commonly understood by one of ordinary skill in the art to which this invention belongs. The terminology used in the description of the invention herein is for the purpose of describing particular embodiments only, and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All publications, patent applications, patents, and other references mentioned herein are incorporated by reference herein in their entirety for all purposes.

As used herein, "a," "an," or "the" can mean one or more than one.

Also, as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20% of the specified amount.

The term "non-sticky" means having a firm, dry, and brittle surface or texture.

The term "substantially gluten free" means total gluten content of the composition is <20 ppm.

The term "substantially sugar free" means each simethicone chewable medicated composition contains less than 0.5 grams of sugar, both natural and added.

The term "chewable medicated composition" may be used interchangeably with gummies, gummy bears, gum drops, jelly candy, gummi chews, chewable gels, chew gels, soft chews, gummy candy, gummies, jelly fruit candy, confectionery or jellies. To be clear, the chewable medicated composition of the present invention does not include conventional compressed dosage forms such as tablets, chewable tablets and capsules.

The present invention is further illustrated by reference to the following examples which is for illustrative purposes only, and does not limit the scope of the invention in any manner.

Example 1

| Ingredient | Quantity (% w/w) | |
|---|---|---|
| | Example 1A | Example 1B |
| Simethicone emulsion USP | 10 | 12 |
| Organic cane sugar | 30 | 35 |
| Organic tapioca syrup | 30 | 35 |
| Carrageenan | 0.1 | 2 |
| Citric acid | 0.1 | 1.5 |
| Trisodium citrate | 0.1 | 1.5 |
| Coloring agent | 0.1 | 1 |
| Flavoring agent | 0.1 | 2 |
| Water | 5 | 10 |

The chewable composition was obtained by the following manufacturing process—

Purified Water was added into cookers and heated for about 45 to about 60 minutes at boiling point. Carrageen was then added to it and mixed well at about 100 to about 105° C. for about 10 to about 15 minutes, until all was dissolved and no lumps remained. This was followed by addition of Organic Tapioca Syrup, and mixing was continued for about 3 to about 5 minutes at about 70° C. to about 80° C. Organic Cane Sugar and inulin were then added, and mixing was continued for another 5 to 10 minutes at about 85° C. to about 90° C. Trisodium citrate was added to the mass at about 75° C. to about 85° C. while mixing at about 75° C. to about 85° C. for about 5 to about 15 minutes. The Gummy Brix thus obtained was cooked for about 45 to about 60 minutes, at about 80° C. to about 100° C., and a Refractometer setpoint of 65 to 70%. The gummy Brix was then transferred holding tanks, and the temperature of cookers to was reduced to about 125° C. Simethicone was then added slowly with mixing, followed by addition of color, flavors, and citric acid and mixed for another 5 to 10 minutes. Subsequent to this, the gummy Brix was transferred to hoppers, and the hoppers were pumped up to 20 times. The hopper pistons were adjusted so that the gummy Brix flows smoothly and fills moulds. Finally, the product was left at room temperature for about 2 to about 24 hours, and then packed into bottles or blisters.

Example 2

| Ingredient | Quantity (% w/w) | |
| --- | --- | --- |
| | Example 2A | Example 2B |
| Simethicone emulsion USP | 11 | 12 |
| Organic cane sugar | 12 | — |
| Monk fruit sweetener | 9 | 22 |
| Inulin | 2 | 9 |
| Organic allulose syrup | 15 | 17 |
| Organic tapioca syrup | 15 | 17 |
| Carrageenan | 0.1 | 2 |
| Citric acid | 0.1 | 1.5 |
| Trisodium citrate | 0.1 | 1.5 |
| Coloring agent | 0.1 | 1 |
| Flavoring agent | 0.1 | 2 |
| Water | 5 | 10 |

The chewable composition was obtained by a process similar to that disclosed in Example 1 above.

Example 3

| Ingredient | Quantity (% w/w) |
| --- | --- |
| Simethicone emulsion USP | 11.10 |
| Maltitol | 24.49 |
| Sorbitol | 5.0 |
| Isomalt oligosaccharide | 28.72 |
| Inulin | 6.21 |
| Purified water | 21.73 |
| Carrageenan | 1.32 |
| Trisodium citrate | 0.23 |
| Citric acid anhydrous | 0.16 |
| DL malic acid | 0.08 |
| Coloring agent | 0.03 |
| Flavoring agent | 0.93 |
| Total | 100 |

The chewable composition was obtained by following the manufacturing process detailed below—

Purified Water was added into cookers and heated to boiling point for about 45 to about 60 minutes. Carrageen was then added and mixed well for about 10 to about 15 minutes at about 100° C. to about 105° C., until all was dissolved and no lumps remained. This was followed by addition of Sorbitol and Maltitol syrup, and mixing was continued for another 5 to 15 minutes at about 70° C. to about 90° C. Isomalt oligosaccharide and inulin were then added, and mixing was continued for 5 to 15 minutes at about 85° C. to about 90° C. Trisodium citrate was added to the mass at about 75° C. to about 85° C., while mixing for about 5 to about 15 minutes at the same temperature. The gummy Brix thus obtained was cooked for about 45 to 60 minutes, at 80 to 100° C., and at a refractometer setpoint of 65 to 70%. This was followed by transfer of the gummy Brix to holding tanks. The temperature of cookers was reduced to 125° C. In the holding tanks, Simethicone was added slowly with mixing, and colors, flavors, and citric acid was subsequently added. The mass was mixed for about 5 to 10 minutes, and then transferred to hoppers. The hoppers were pumped up to 20 times and the hopper pistons were adjusted to ensure that the gummy Brix flows smoothly and fills moulds.

Example 4

| Ingredient | Quantity (% w/w) |
| --- | --- |
| Simethicone emulsion USP | 11.10 |
| Maltitol | 29.9 |
| Isomalt Powder | 28.92 |
| Inulin | 5.87 |
| Purified water | 21.57 |
| Carrageenan | 1.09 |
| Pectin | 0.27 |
| Trisodium Citrate | 0.24 |
| Citric Acid Anhydrous | 0.22 |
| Coloring agent | 0.03 |
| Flavoring agent | 0.88 |
| Total | 100 |

The chewable composition was obtained by following the manufacturing process detailed below—

Purified Water was added into cookers and heated to boiling point for about 45 to about 60 minutes. Carrageen and Pectin were then added and mixed well for about 10 to about 15 minutes at about 100° C. to about 105° C., until all was dissolved and no lumps remained. This was followed by addition of Maltitol, and mixing was continued for another 5 to 15 minutes at about 70° C. to about 90° C. Isomalt powder & Inulin were then added, and mixing was continued for 5 to 15 minutes at about 85° C. to about 90° C. Trisodium citrate was added to the mass at about 75° C. to about 85° C., while mixing for about 5 to about 15 minutes at the same temperature. The gummy Brix thus obtained was cooked for about 45 to 60 minutes, at 80 to 100° C., and at a refractometer setpoint of 65 to 70%. This was followed by transfer of the gummy Brix to holding tanks. The temperature of cookers was reduced to 125° C. In the holding tanks, Simethicone was added slowly with mixing, and colors, flavors, and citric acid was subsequently added. The mass was mixed for about 5 to 10 minutes, and then transferred to hoppers. The hoppers were pumped up to 20 times and the hopper pistons were adjusted to ensure that the gummy Brix flows smoothly and fills moulds.

The invention claimed is:
1. A chewable medicated composition comprising
   i. about 10% w/w to about 20% w/w of simethicone as the sole active ingredient, wherein the simethicone is uniformly dispersed in the composition,
   ii. about 0.1% w/w to about 2% w/w of a gelling agent selected from the group consisting of carrageenan, pectin and combinations thereof,
   iii. a sweetening agent,
   iv. a pH adjusting agent in an amount sufficient to provide a pH of about 2.5 to about 6.5,
   V. a flavouring agent,
   vi. a dietary fiber, and
   vii. a coloring agent,
   wherein (a) the composition is substantially free of sugar, and does not contain gelatin or gluten, (b) the total microbial count in the composition remains <1500 CFU/g when stored for at least 18 months at ambient temperature with minimum exposure to sunlight, (c) the composition disintegrates within about 40 minutes or less when tested using the USP <701> Disintegration Test and (d) the chewable medicated composition is a gummy, gummy bear, gum drop, jelly candy, gummy chew, chewable gel, chew gel, soft chew, gummy candy, jelly fruit candy, confectionery or jelly.

2. The chewable medicated composition of claim 1, wherein the simethicone is about 10% w/w to about 15% w/w of the composition.

3. The chewable medicated composition of claim 1, wherein the gelling agent is about 0.1% w/w to about 1% w/w of the composition.

4. The chewable medicated composition of claim 1, wherein the sweetening agent comprises a nutritive agent, a non-nutritive agent or combinations thereof.

5. The chewable medicated composition of claim 4, wherein the sweetening agent is a nutritive agent comprising dextrose, fructose, sucrose, agave nectar, brown rice syrup, date sugar, honey, molasses and blackstrap molasses, sorghum syrup, stevia, maple syrup, birch syrup, yacon syrup, lucuma powder, coconut sugar, erythritol, maltitol, mannitol, sorbitol, xylitol, isomalt, lactitol, maltitol or combinations thereof.

6. The chewable medicated composition of claim 4, wherein the sweetening agent is a non-nutritive sweetening agent comprising acesulfame, advantame, alitame, aspartame, neotame, saccharin, sodium saccharin, sucralose, acesulfame potassium, thaumatin, stevioside or combinations thereof.

7. The chewable medicated composition of claim 1, wherein the pH adjusting agent comprises a buffering agent comprising citric acid, succinic acid, fumaric acid, tartaric acid, phosphoric acid, boric acid, ascorbic acid, pharmaceutically acceptable salts thereof or combinations thereof.

* * * * *